United States Patent [19]

Kubo et al.

[11] Patent Number: 6,156,797

[45] Date of Patent: Dec. 5, 2000

[54] PERITONEAL DIALYSIS SOLUTION

[75] Inventors: Akihiro Kubo; Hiroaki Takahashi; Kazuo Chiku; Hidehiko Ooshima; Shinsuke Kawai; Teruyuki Usui; Yasuhiko Fukuta, all of Kanagawa, Japan

[73] Assignee: Terumo Kabushiki Kaisha, Tokyo, Japan

[21] Appl. No.: 09/348,496

[22] Filed: Jul. 7, 1999

[30] Foreign Application Priority Data

Jul. 7, 1998 [JP] Japan .................................. 10-191584

[51] Int. Cl.⁷ .......................... A61K 31/19; A61K 33/14
[52] U.S. Cl. ............................. 514/557; 424/663
[58] Field of Search .............................. 514/557; 424/663

[56] References Cited

U.S. PATENT DOCUMENTS 5,011,826  4/1991  Steudle et al. .......................... 514/23
5,670,176  9/1997  Martis et al. .......................... 424/663
5,698,230  12/1997  Martis et al. .......................... 424/663

*Primary Examiner*—Theodore J. Criares
*Assistant Examiner*—Jennifer Kim
*Attorney, Agent, or Firm*—Burns, Doane, Swecker & Mathis, LLP

[57] ABSTRACT

A peritoneal dialysis solution comprising at least one cation, a chloride ion contained at a concentration differing from a concentration of total cation so that the concentration of chloride ion will be lower than the concentration of total cation, and organic acids contained so as to maintain electrical neutrality depending on a difference in concentration between the total cation and chloride ion, the concentration of organic acids satisfies a predetermined equation. Also, disclosed is a method for adjusting a peritoneal dialysis solution, comprising providing a difference in concentration between total cation and chloride ion, adding organic acids so as to maintain electrical neutrality, and adjusting dialyzing performance depending on a degree of the difference in concentration and/or kind of organic acid added.

5 Claims, 5 Drawing Sheets

PERITONEAL DIALYSIS SOLUTION

BACKGROUND OF THE INVENTION

1. Field of the Invention

The present invention belongs to the technical field of peritoneal dialysis solution used in peritoneal dialysis therapy.

2. Description of the Related Art

One of allopathies for end-stage renal failure includes peritoneal dialysis therapy.

The principle of this therapy is to inject a peritoneal dialysis solution having an osmotic pressure higher than that of body fluid into the peritoneal cavity and utilize a difference in osmotic pressure between the body fluid (blood) and peritoneal dialysis solution across peritoneum to remove moisture from the body (to remove water by ultrafiltration). Removal of uremic toxins (urea, creatinine, phosphorus, etc.) is performed mainly by diffusion but the removal of those substances is also performed by transport of water upon ultrafiltration (convection).

Peritoneal dialysis therapy, which has to be practiced continuously for a long term, has various advantages in that it does not require large apparatus and instruments, requires less time, needs less therapeutic cost, and is advantageous in patient's coming back to the society or home treatment, and in addition that the decrease in patient's renal function can be reduced, as compared with hemodialysis therapy.

At present, peritoneal dialysis solution clinically applied to peritoneal dialysis therapy comprises generally an electrolyte (sodium ion, calcium ion, magnesium ion, chloride ion, etc.), an alkalizing agent (usually lactate ion), an osmoregulatory substance (osmotic agent, usually glucose).

SUMMARY OF THE INVENTION

In such a peritoneal dialysis solution, the efficiency of dialysis (net ultrafiltration volume and amount of removed uremic toxins) is controlled by varying the concentration of osmotic agent, i.e., glucose so as to increase or decrease the osmotic pressure with keeping the compositions of electrolytes and alkalizing agent constant.

To increase the efficiency of dialysis, there has been taken a technique for increasing osmotic pressure (osmolity i.e., concentration of glucose). However, this technique has the following problems.

(1) An increase of glucose concentration causes obesity in dialysis patients and in addition gives adverse reactions on blood vessel lesion of diabetic renal failure patients whose number has been increasing in recent years.

(2) An increase of osmotic pressure accelerates a reduction of peritoneal function and as a result, it raises clinical problems that dialysis becomes impossible and the patients have to leave the therapy and so on.

Therefore, conventional peritoneal dialysis solutions which controls efficiency of dialysis by adjusting glucose concentration has a problem in which it is difficult to continue a long-term therapy. For this reason, the development of a novel peritoneal solution which can give more effective dialysis without increasing osmotic pressure has been in demand.

An object of the present invention is to solve the above-mentioned problems of the prior art and provide a peritoneal dialysis solution and a method for adjusting it which can increase the net ultrafiltration volume, prolong time for transport of water (dwell time), reduce the dose of peritoneal dialysis solution, decrease glucose load, and continue long-term peritoneal dialysis therapy without increasing osmotic pressure (glucose concentration) or with further decreasing osmotic pressure.

As described above, peritoneal dialysis solutions using glucose as the osmotic agent have problems that they give adverse reactions on blood vessel lesion of diabetic renal failure patients, accelerate a reduction in peritoneum function so that dialysis becomes impossible and the patients have to leave the therapy, and so on.

To solve such problems, various studies and developments have been made for peritoneal dialysis solutions that can give effective dialysis at a decreased osmotic pressure (glucose concentration). These studies and developments have been conducted mainly by testing osmotic agents other than glucose. For example, in order to increase the efficiency of dialysis without increasing the osmotic pressure, there have been tried methods in which substances of high molecular weights such as dextrin, maltose or the like were used as an osmotic agent.

On the contrary, the present inventors have made intensive investigation on a peritoneal dialysis solution that can give higher effect of dialysis and consequently have found that a technique different from the study of substitute osmotic agents as conventionally made, that is, provision of a difference in concentration between the total cation and chloride ion contained in peritoneal dialysis solution, electrical neutralization of the difference in concentration with an organic acid, and adjusting the concentration of organic acid to a predetermined value depending on the carbon number of organic acid can realize a peritoneal dialysis solution having excellent dialysis effects such as an increase in net ultrafiltration volume, a prolonged time for transport of water, etc. without resort to osmotic pressure and that selection of the difference in concentration and/or selection of organic acid contained can adjust the dialysis effects, thereby completing the present invention.

That is, the present invention provides a peritoneal dialysis solution comprising at least one cation, a chloride ion contained at a concentration differing from a concentration of total cation so that the concentration of chloride ion will be lower than the concentration of total cation, and an organic acid contained so as to maintain electrical neutrality depending on a different in concentration between the total cation and chloride ion, the concentration of organic acid satisfies the following equation $$A/60+B/50+C/40+D/30+E/20+F/10 \geq 1$$

wherein A (mmol/l) is a total concentration of organic acid having 3 carbon atoms, B (mmol/l) is a total concentration of organic acid having 4 carbon atoms, C (mmol/l) is a total concentration of organic acid having 5 carbon atoms, D (mmol/l) is a total concentration of organic acid having 6 carbon atoms, E (mmol/l) is a total concentration of organic acid having 7 carbon atoms, and F (mmol/l) is a total concentration of organic acid having 8 or more carbon atoms.

In the above equation, A, B, C, D, E, and F may dependently be 0.

The concentration of chloride ion is preferably 30 mEq/l to 180 mEq/l, more preferably 50 mEq/l to 180 mEq/l.

The osmotic pressure of peritoneal dialysis solution is preferably 260 mOsm/kg to 600 mOsm/kg, more preferably 270 mOsm/kg to 600 mOsm/kg.

The peritoneal dialysis solution may further comprise a reducing sugar.

Also, the present invention provides a method for adjusting a peritoneal dialysis solution, comprising providing a difference in concentration between total cation and chloride ion, adding an organic acid so as to maintain electrical neutrality depending on the difference in concentration, and adjusting dialyzing performance depending on a degree of the difference in concentration and/or kind of organic acid added.

DETAILED DESCRIPTION OF THE INVENTIION

Figure 1:
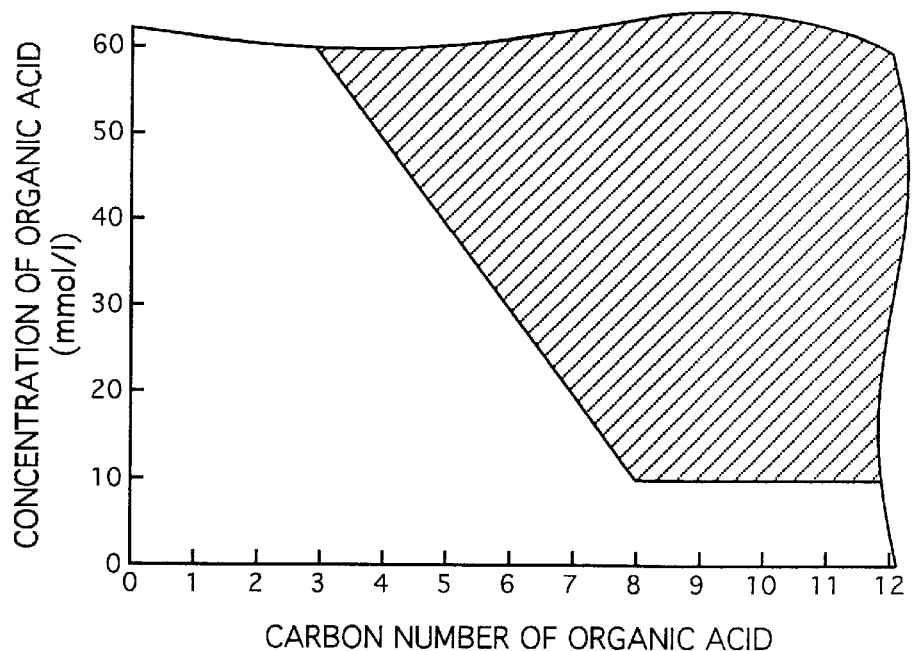
FIG. 1 is a graph illustrating the relationship between the carbon number and preferred content of organic acid contained in peritoneal dialysis solution of the present invention.

Hereafter, the peritoneal dialysis solution and a method for adjusting a peritoneal dialysis solution according to the present invention will be described in detail.

The peritoneal dialysis solution includes as a basic construction provision of a difference in concentration between the total cation and chloride ion and containing organic acids for the electrical neutralization of the difference in concentration depending on the difference in concentration, whereby the present invention can realize an increase in the net ultrafiltration volume and a prolonged time for transport of water (that is, effective dialysis time) and obtain excellent dialysis effect.

In such a peritoneal dialysis solution of the present invention, the cation contained is the same as in usual peritoneal dialysis solutions and includes, for example, sodium ion, calcium ion, magnesium ion, etc.

The concentration of cation is not limited particularly but the concentration of sodium ion is preferably 100 to 200 mEq/l, more preferably 130 to 150 mEq/l. The concentration of calcium ion is preferably 0 to 5 mEq/l, more preferably 1 to 5 mEq/l. Further, the concentration of magnesium ion is preferably 0 to 5 mEq/l, more preferably 0.5 to 2 mEq/l.

On the other hand, the concentration of chloride ion is not limited particularly so long as it is set to be lower than the concentration of total cation but is preferably 30 to 180 mEq/l, further more preferably 70 to 110 mEq/l.

As will be later on, the difference in concentration between total cation and chloride ion is determined properly depending on the targeted dialyzing effect (net ultrafiltration volume, dwell time, amount of removed uremic toxins, etc.) and organic acids used and is not limited particularly.

Each of the ions may be caused to be contained in the peritoneal dialysis solution of the present invention in the same manner as in usual peritoneal dialysis solutions using sodium chloride, calcium chloride, magnesium chloride, and sodium, calcium, magnesium, etc. salts of organic acids such as sodium lactate.

In the present invention, a difference in concentration is provided between total cation and chloride ion and an organic acid is contained to maintain electrical neutrality depending on the difference in concentration. The organic acid is not limited particularly but preferably an organic acid having 3 or more carbon atoms is used.

Here, according to the examples and study by the present inventors, the peritoneal dialysis solution of the present invention exhibit good dialyzing effect when it contains an organic acid in an amount of 60 mmol/l or more in the case of an organic acid having 3 carbon atoms, in an amount of 50 mmol/l or more in the case of an organic acid having 4 carbon atoms, in an amount of 40 mmol/l or more in the case of an organic acid having 5 carbon atoms, in an amount of 30 mmol/l or more in the case of an organic acid having 6 carbon atoms, in an amount of 20 mmol/l or more in the case of an organic acid having 7 carbon atoms, and in an amount of 10 mmol/l or more in the case of an organic acid having 8 or more carbon atoms. That is, when the content of organic acid is set in the shaded region in FIG. 1, good dialyzing effect can be obtained.

Therefore, in the present invention, the concentration of organic acids in the peritoneal dialysis solution satisfies the following equation $$A/60+B/50+C/40+D/30+E/20+F/10 \geq 1$$

wherein A (mmol/l) is a total concentration of organic acid having 3 carbon atoms, B (mmol/l) is a total concentration of organic acid having 4 carbon atoms, C (mmol/l) is a total concentration of organic acid having 5 carbon atoms, D (mmol/l) is a total concentration of organic acid having 6 carbon atoms, E (mmol/l) is a total concentration of organic acid having 7 carbon atoms, and F (mmol/l) is a total concentration of organic acid having 8 or more carbon atoms.

As described above, in the present invention, the organic acid is blended in order to maintain electrical neutrality of peritoneal dialysis solution. Therefore, the total content of organic acid depends on the difference in concentration between the total cation and chloride ion. If the concentration of chloride ion is set at too low a level, then there is the fear that the blood electrolyte level balance will be disturbed so that the difference in concentration between the total cation and chloride ion must be within a certain range. Accordingly, the total content of organic acids is preferably 110 mmol/l or less, more preferably 100 mmol/l or less.

Here, as will be apparent from FIG. 1 and the above-mentioned equation, the present invention provides more excellent dialyzing effect, as the number of carbons of the organic acid is longer. Also, the greater the difference in concentration between the total cation and chloride ion (the larger the content of organic acid) is, the more excellent dialyzing effect can be obtained.

Therefore, according to the present invention, a peritoneal dialysis solution can be obtained which not only has a high dialyzing effect but also matches the targeted dialyzing effect by properly selecting and setting difference in concentration between the total cation and chloride ion, organic acids to be contained, and the like.

For example, when more excellent dialyzing effect such as a large net ultrafiltration volume is needed, the difference in concentration between the total cation and chloride ion may be set large and/or organic acids having a larger carbon number may be used.

Further, even when the above-mentioned difference in concentration cannot be set greater (the amount of chloride ion cannot be decreased relative to cations) depending on the state of patient's disease and so on, use of higher carbon number organic acids such as having 8 carbon atoms enables one to obtain excellent dialyzing effect. That is, even when the difference in concentration between the total cation and chloride ion is small, excellent dialyzing effect can be obtained by selecting an organic acid.

On the contrary, when it is preferred to set the content of chloride ion to be smaller than the total cation (larger cation content) but a ultrafiltration which is superior to the conventional peritoneal dialysis solution to some extent is sufficient depending on the state of patient's disease and so on, then organic acids having smaller number of carbon atoms may be used.

That is, according to the present invention, the balance between cation and chloride ion can be adjusted while securing excellent dialyzing effect depending on the state of patient's disease and so on.

Moreover, according to the present invention, such increase or adjustment of dialyzing effect as described above can be realized regardless of the osmotic pressure of peritoneal dialysis solution. Therefore, the peritoneal dialysis solution provides a sufficiently excellent dialyzing effect at an osmotic pressure lower than that of the conventional peritoneal dialysis solution or if it is at the same osmotic pressure, it provides a higher dialyzing effect than that of the conventional peritoneal dialysis solution.

Further, according to the present invention in which a difference in concentration is provided between the total cation and chloride ion and electrical neutrality is maintained with an organic acid, load to patient by glucose (amount of incorporation into the body) can be decreased even when the peritoneal dialysis solution contains a large amount of glucose.

In the present invention, the organic acid to be used is not limited particularly but various mono- or poly-functional organic acids can be utilized.

Preferably mono-functional organic acid may be utilized since more amount of moles can be included in the dialysis solution.

As an example, the organic acid having 3 carbon atoms includes preferably lactic acid, propionic acid, etc.; the organic acid having 4 carbon atoms include preferably malic acid, fumaric acid, succinic acid, oxaloacetic acid, N-acetylglycine, etc.; the organic acid having 5 carbon atoms includes preferably N-acetyl-L-cystein, glutaric acid, etc.; the organic acid having 6 carbon atoms includes preferably glucuronic acid, ascorbic acid, citric acid, isocitric acid, gluconic acid, N-acetyl-L-aspartic acid, etc.; the organic acid having 7 carbon atoms includes preferably N-acetyl-L-glutamic acid, N-acetyl-L-methionine, N-acetyl-L-proline, N-acetyl-L-valine, etc.; the organic acid having 8 or more carbon atoms includes preferably, N-acetyl-L-arginine, N-acetyl-L-histidine, N-acetyl-L-leucine, N-acetyl-L-tryptophane, etc.

In the present invention, such organic acids may be used singly or a plurality of species differing in the number of carbon or a plurality of species having the same number of carbon atoms or both of them may be used.

Therefore, in the present invention any one of the following is satisfied:

A/60≧1, B/50≧1, C/40≧1, D/30≧1, E/20≧1, F/10≧1, A60+B/50≧1, A/60+C/40≧1, A/60+D/30≧1, A/60+E/20≧1, A/60+F/10≧1, B/50+C/40≧1, B/50+D/30≧1, B/50+E/20≧1, B/50+F/10≧1, C/40+D/30≧1, C/40+E/20≧1, C/40+F/10≧1, D/30+E/20≧1, D/30+F/10≧1, E/20+F/10≧1, A60+B/50+C/40≧1, A60+B/50+D/30≧1, A60+B/50+E/20≧1, A60+B/50+F/10≧1, A60+C/40+D/30≧1, A60+C/40+E/20≧1, A60+C/40+F/10≧1, A60+D/30+E/20≧1, A60+D/30+F/10≧1, A60+E/20+F/10≧1, B/50+C/40+D/30≧1, B/50+C/40+E/20≧1, B/50+C/40+F/10≧1, B/50+D/30+E/20≧1, B/50+D/30+F/10≧1, B/50+E/20+F/10≧1, C/40+D/30+E/20≧1, C/40+D/30+F/10≧1, C/40+E/20+F/10≧1, D/30+E/20+F/10≧1, A60+B/50+C/40+D/30≧1, A60+B/50+C/40+E/20≧1, A60+B/50+C/40+F/10≧1, A60+B/50+D/30+E/20≧1, A60+B/50+D/30+F/10≧1, A60+B/50+E/20+F/10≧1, A60+C/40+D/30+E/20≧1, A60+C/40+D/30+F/10≧1, A60+C/40+E/20+F/10≧1, A60+D/30+E/20+F/10≧1, B/50+C/40+D/30+E/20≧1, B/50+C/40+D/30+F/10≧1, B/50+C/40+E/20+F/10≧1, B/50+D/30+E/20+F/10≧1, C/40+D/30+E/20+F/10≧1, A/60+B/50+C/40+D/30+E/20≧1, A/60+B/50+C/40+D/30+F/10≧1, A/60+B/50+C/40+E/20+F/10≧1, A/60+B/50+D/30+E/20+F/10≧1, A/60+C/40+D/30+E/20°F/10≧1, B/50+C/40+D/30+E/20+F/10≧1, and A/60+B/50+C/40+D/30+E/20+F/10≧1.

Also, organic acid salts containing these organic acid ions such as sodium salt can be utilized advantageously.

The peritoneal dialysis solution of the present invention may if needed contain osmotic agents used in usual peritoneal dialysis solutions.

An example of the osmotic agent can be used a reducing sugar because of its safety for living body as used in the prior art. Examples of the reducing sugar include glucose, dextrin, maltose, etc.

Their content is not limited particularly but, for example, in the case of glucose, it is preferably in the range of 0 to 4.0 g/dl.

They may be selected properly depending on the osmotic pressure and pH of the peritoneal dialysis solution, the state of patient, and so on.

The pH of the peritoneal dialysis solution of the present invention is preferably 5.0 to 8.0, more preferably 5.5 to 7.5. The osmotic pressure is preferably 260 to 600 mOsm/kg, more preferably 260 to 600 mOsm/kg, further more preferably 280 to 500 mOsm/kg.

The adjustment method may be performed by a known method.

The peritoneal dialysis solution of the present invention can be prepared by dissolving the above-mentioned cation and chloride ion sources, organic acids and other components in water.

The prepared peritoneal dialysis solution is desirably included in a soft plastic bag or a glass container before it can be subjected to high pressure steam sterilization or hot water sterilization. The material for soft plastic includes polyvinyl chloride, polypropylene, polyethylene, polyester, polyamide, ethylene vinyl alcohol copolymer, polyethylene terephthalate, polyvinylidene chloride, ethylene vinyl acetate copolymer, etc. It may be a combination of them as a multilayer film.

Note that the method of using the peritoneal dialysis solution of the present invention is not limited in any way but it may be used by the technique of a known peritoneal dialysis therapy.

As described above and will be apparent from the examples hereinbelow, the peritoneal dialysis solution of the present invention can increase the net ultrafiltration volume and prolong dwell time as compared with peritoneal dialysis solution generally applied to clinical use under the conditions where the osmotic pressure and injection amount are the same. Further, when glucose is contained, its amount of incorporation into the body can be decreased.

Therefore, use of the peritoneal dialysis solution of the present invention can decrease the injection amount into intraperitoneal cavity as compared with the conventional peritoneal dialysis solution so that the selectivity of the time for exchanging the dialysate can be extended. Therefore, the frequency for exchanging the dialysate can be reduced. That is, according to the present invention, miniaturization (down-sizing) of a bag containing a peritoneal dialysis solution, a reduction in space for storing peritoneal dialysis solution bags, and a decrease in amount of wastes are possible.

To patients for whom the net ultrafiltration volume is sufficiently secured, it is possible to decrease the osmotic pressure, for example, by decreasing the concentration of glucose as the osmotic agent so that it is possible to continue the therapy for a long term without a load to the peritoneum.

In addition, since the present invention can decrease the amount of glucose absorbed into the body, the peritoneal dialysis solution of the present invention is advantageous to peritoneal dialysis therapy of patients suffering from lipid pathobolism, obesity, diabetes, etc.

Therefore, the present invention can contribute much to the coming back to the society and QOL (quality of life) of patients.

EXAMPLES

Hereafter, the present invention will be described in detail by specific examples of the present invention.

Example 1

Study on the effect of difference in concentration between the total cation and chloride ion on the net ultrafiltration volume (Preparation of peritoneal dialysis solutions)

Sodium chloride and sodium lactate were dissolved in water for injection so that the electrolyte ions and organic acid ion would be of the concentrations shown in Table 1 to obtain peritoneal dialysis solutions of Example 1 of the invention and Comparative Examples 1 and 2. Note that the osmotic pressure was measured with a pH-osmometer (HOSM-1, manufactured by Toa Denpa Kogyo Co., Ltd.) The osmotic pressures in the following examples were measured in the same manner as in this example.

TABLE 1

|  | Comparative Example 1 | Comparative Example 2 | Example 1 |
|---|---|---|---|
| Na$^-$ (mEq/l) | 140 | 140 | 140 |
| Cl$^-$ (mEq/l) | 140 | 90 | 40 |
| Lactate ion (mmol/l) | 0 | 50 | 100 |
| Osmotic pressure (mOsm/kg) | 265 | 265 | 265 |

(Peritoneal Dialysis Test)

For each of the peritoneal dialysis solutions shown in Table 1, the following peritoneal dialysis tests were carried out using rats.

Male Sprague-Dawley (SD) rats weighing about 200 g were preliminary bred for 6 days and then starved for 24 hours before they were used in the test. During the preliminary breeding period, food and water were given freely and during the starvation only water was given freely. The test was conducted under ether anesthesia but during the dialysis the rats were awaken.

After measuring body weight A (g) just before administration of a peritoneal dialysis solution, a peritoneal dialysis solution (40 ml/kg) was administered intraperitoneally using a 24 G syringe. After the administration, body weight B (g) was measured immediately and dialysis was started. After a fixed dwell time, body weight C (g) was measured and immediately peritoneotomy was operated and the dialysate was completely removed with a syringe and absorbent cotton followed by measurement of body weight D (g).

The net ultrafiltration volume (mg/kg) was obtained by the following equation taking the specific gravity of the dialysate as unity.

Net ultrafiltration volume (ml/kg)=[(C−D)−(B−A)]/A×1000

(Results)

Figure 2:
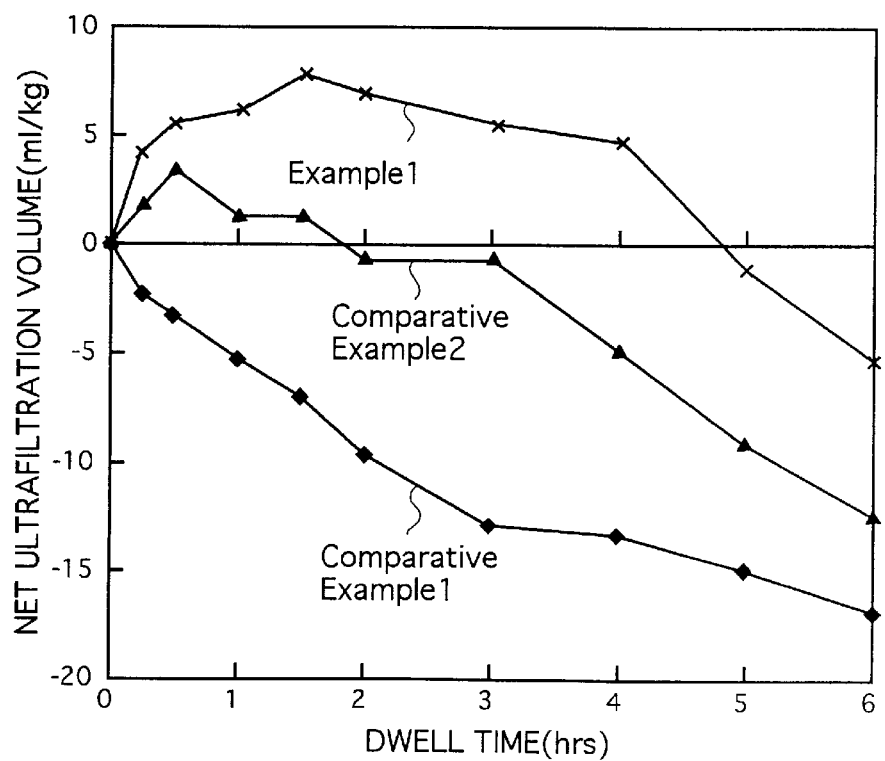
FIG. 2 is a graph illustrating the effect of peritoneal dialysis solution of the present invention.

The changes in the net ultrafiltration volume in the above-mentioned peritoneal dialysis tests are shown in FIG. 2.

The results indicated that Example 1 gave larger net ultrafiltration volume at any pool time than Comparative Examples 1 and 2. The similar effect was observed in other organic acids.

The results demonstrated that in spite of the peritoneal dialysis solutions at the same osmotic pressure (265 mOsm/kg), prolongation of the dwell time in addition to an increase in the net ultrafiltration volume could be obtained by rendering the difference in concentration between total cation and chloride ion greater and maintaining electrical neutrality with an organic acid.

Example 2

Study on the effect of difference in concentration between the total cation and chloride ion on the net ultrafiltration volume when the peritoneal dialysis solution contains glucose.

(Preparation of a Peritoneal Dialysis Solution and Peritoneal Dialysis Test)

Glucose, sodium chloride, and sodium lactate were dissolved in water for injection so that the reduced sugar, electrolyte ions, and organic acid ion would be of the concentrations shown in Table 2 to obtain peritoneal dialysis solutions of Example 2 of the invention and Comparative Examples 3 and 4. As will be apparent from Table 2, the peritoneal dialysis solutions here had the same compositions in which glucose was added to the peritoneal dialysis solutions shown in Table 1 at concentration of 1.35 W/V %. "W/V %" herein means the number of grams of glucose (osmotic agent) per 100 milliliters (100 ml) of peritoneal dialysis solution.

The prepared peritoneal dialysis solutions were subjected to peritoneal dialysis test in the same manner as in Example 1.

TABLE 2

|  | Comparative Example 3 | Comparative Example 4 | Example 2 |
|---|---|---|---|
| Glucose (W/V %) | 1.35 | 1.35 | 1.35 |
| Na$^+$ (mEq/l) | 140 | 140 | 140 |
| Cl$^-$ (mEq/l) | 140 | 90 | 40 |
| Lactate ion (mmol/l) | 0 | 50 | 100 |
| Osmotic pressure (mOsm/kg) | 344 | 344 | 344 |

(Results)

Figure 3:
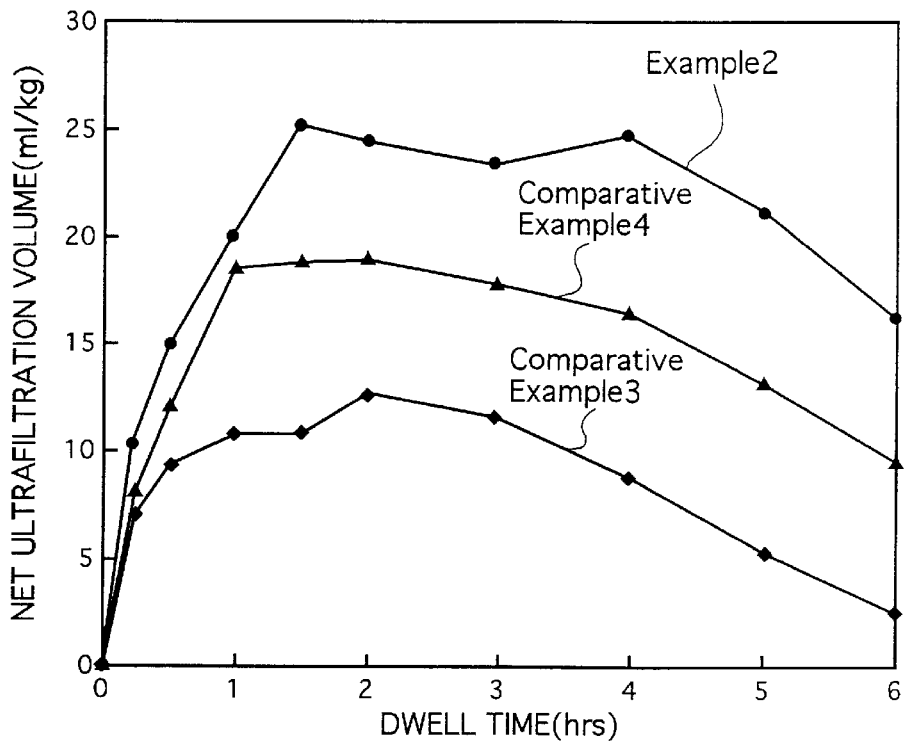
FIG. 3 is a graph illustrating the effect of peritoneal dialysis solution of the present invention.

The changes in the net ultrafiltration volume in the above-mentioned peritoneal dialysis tests are shown in FIG. 3.

The results indicated that Example 2 gave larger net ultrafiltration volume at any dwell time than Comparative Examples 3 and 4. The similar effect was observed in other osmotic agents and in other organic acids.

The results demonstrated that even in the case of peritoneal dialysis solutions containing an osmotic agent to increase the osmotic pressure thereof, prolongation of the dwell time for water removal in addition to an increase in the net ultrafiltration volume could be obtained by rendering the difference in concentration between the total cation and chloride ion greater and maintaining electrical neutrality with an organic acid.

Example 3

Study on the effect of difference in concentration between the total cation and chloride ion on the net ultrafiltration volume when the osmotic pressure is increased with electrolytes
(Preparation of Peritoneal Dialysis Solutions and Peritoneal Dialysis Test).

Sodium chloride and sodium lactate were dissolved in water for injection so that the electrolyte ions and organic acid ion would be of the concentrations shown in Table 3 to obtain peritoneal dialysis solutions of Examples 1, 3 and 4 of the invention and Comparative Examples 1, 5 and 6.

The prepared peritoneal dialysis solutions were subjected to peritoneal dialysis tests in the same manner as in Example 1. Example 1 of the invention, Example 3 and Example 4 of the invention were compared with Comparative Example 1, Comparative Example 5 and Comparative Example 6, respectively.

TABLE 3

| | Comparative Example 1 | Comparative Example 5 | Comparative Example 6 |
|---|---|---|---|
| $Na^+$ (mEq/l) | 140 | 170 | 200 |
| $Cl^-$ (mEq/l) | 140 | 170 | 200 |
| Lactate ion (mmol/l) | 0 | 0 | 0 |
| Osmotic pressure (mOsm/kg) | 265 | 320 | 374 |

| | Example 1 | Example 3 | Example 4 |
|---|---|---|---|
| $Na^+$ (mEq/l) | 140 | 170 | 200 |
| $Cl^-$ (mEq/l) | 40 | 70 | 100 |
| Lactate ion (mmol/l) | 100 | 100 | 100 |
| Osmotic pressure (mOsm/kg) | 265 | 320 | 374 |

Figure 4:
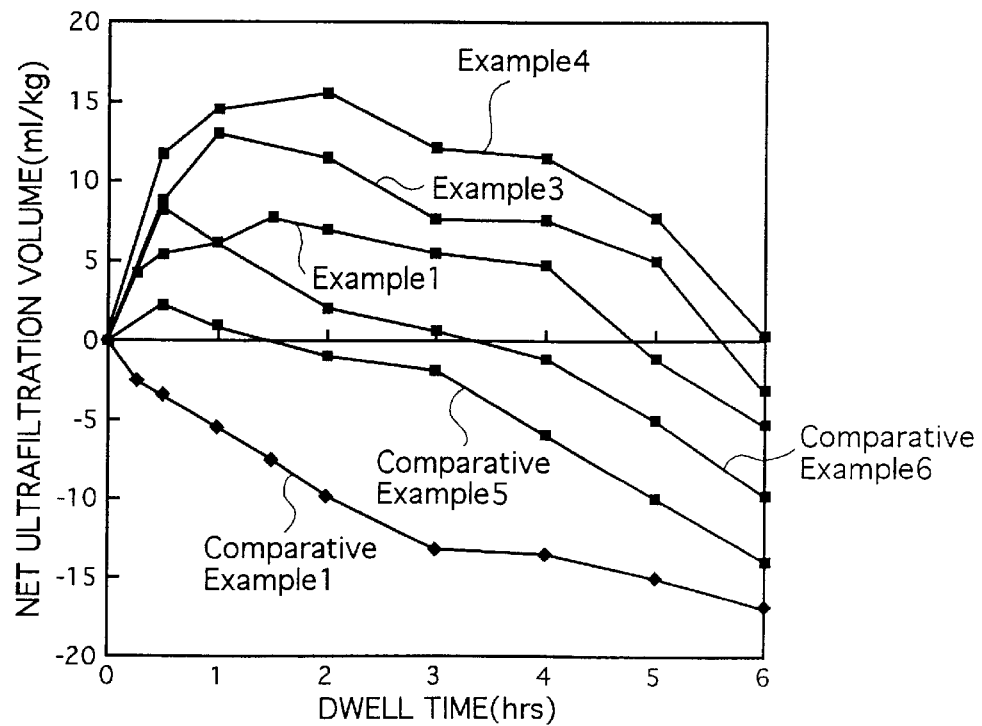
FIG. 4 is a graph illustrating the effect of peritoneal dialysis solution of the present invention.

The changes in the net ultrafiltration volume in the above-mentioned peritoneal dialysis tests are shown in FIG. 4.

The results indicated that Examples 1, 3 and 5 gave larger net ultrafiltration volume at any dwell time than Comparative Examples 1, 5 and 6, respectively. The similar effect was observed in other organic acids and when an osmotic agent was added.

The results demonstrated that even in the case of peritoneal dialysis solutions whose osmotic pressure was increased with electrolyte but glucose, prolongation of the dwell time in addition to an increase in the net ultrafiltration volume could be obtained by rendering the difference in concentration between the total cation and chloride ion greater and maintaining electrical neutrality with an organic acid.

Example 4

Study on the effect of difference in concentration between the total cation and chloride ion and the kind of organic acid (organic acid alone) on the net ultrafiltration volume (Preparation of Peritoneal Dialysis Solutions)

Glucose, sodium chloride, sodium lactate (number of carbon: 3), ascorbic acid (number of carbon: 6), N-acetyl-L-proline (number of carbon: 7), and sodium hydroxide were dissolved in water for injection so that the reduced sugar, electrolyte ions, and organic acid ions would be of the concentrations shown in Table 4 to obtain peritoneal dialysis solutions of Examples 5 to 10 of the invention and Comparative Examples 7 to 12. The Examples and Comparative Examples were practiced using peritoneal dialysis solutions containing 1.35 W/V % and 2.5 W/V % glucose.

TABLE 4

| | Example 5 Comparative Example 7 | Example 6 Comparative Example 8 | Example 7 Comparative Example 9 |
|---|---|---|---|
| Glucose (W/V %) | 1.35 | 1.35 | 1.35 |
| $Na^+$ (mEq/l) | 140 | 140 | 140 |
| $Cl^-$ (mEq/l) | 140–40 | 140–40 | 140–40 |
| Lactate ion (mmol/l) | 0–100 | 0 | 0 |
| Ascorbic acid ion (mmol/l) | 0 | 0–100 | 0 |
| N-Acetyl-L-proline ion (mmol/l) | 0 | 0 | 0–100 |
| Osmotic pressure (mOsm/kg) | 344 | 344 | 344 |

| | Example 8 Comparative Example 10 | Example 9 Comparative Example 11 | Example 10 Comparative Example 12 |
|---|---|---|---|
| Glucose (W/V %) | 2.5 | 2.5 | 2.5 |
| $Na^+$ (mEq/l) | 140 | 140 | 140 |
| $Cl^-$ (mEq/l) | 140–40 | 140–40 | 140–40 |
| Lactate ion (mmol/l) | 0–100 | 0 | 0 |
| Ascorbate ion (mmol/l) | 0 | 0–100 | 0 |
| N-Acetyl-L-proline ion (mmol/l) | 0 | 0 | 0–100 |
| Osmotic pressure (mOsm/kg) | 416 | 416 | 416 |

The peritoneal dialysis solutions of Examples 5 to 10 and Comparative Examples of 7 to 12 were subjected to peritoneal dialysis tests in the same manner as in Example 1. In the Examples and Comparative Examples, the net ultrafiltration volume, glucose absorption ratio (Examples 5 to 7 and Comparative Examples 7 to 9) after 6-hour dwell time of each peritoneal dialysis solution were compared and studied. The glucose absorption ratio was measured by the following method.

(Measurement of Glucose Absorption Ratio)

The concentration of glucose in the dialysate obtained in the peritoneal dialysis tests was measured and glucose absorption ratio was obtained according to equations 2 to 5 below.

Amount of administered glucose (mg/kg)=[concentration of glucose in the administered peritoneal dialysis solution (mg/dl)× administered solution volume (body weight B−body weight A) (ml)]/body weight A×1000/100      Equation 2

Amount of residual glucose (mg/kg)=[concentration of glucose in dialysate (mg/dl)×dialysate volume (body weight C−body weight D) (ml)]/body weight A×1000/100      Equation 3

Amount of absorbed glucose (mg/kg)=[amount of administered glucose (mg/kg)−amount of residual glucose (mg/kg)      Equation 4

Glucose absorption ratio (%)=amount of absorbed glucose/amount of administered glucose (mg/kg)×100      Equation 5

Figure 5:
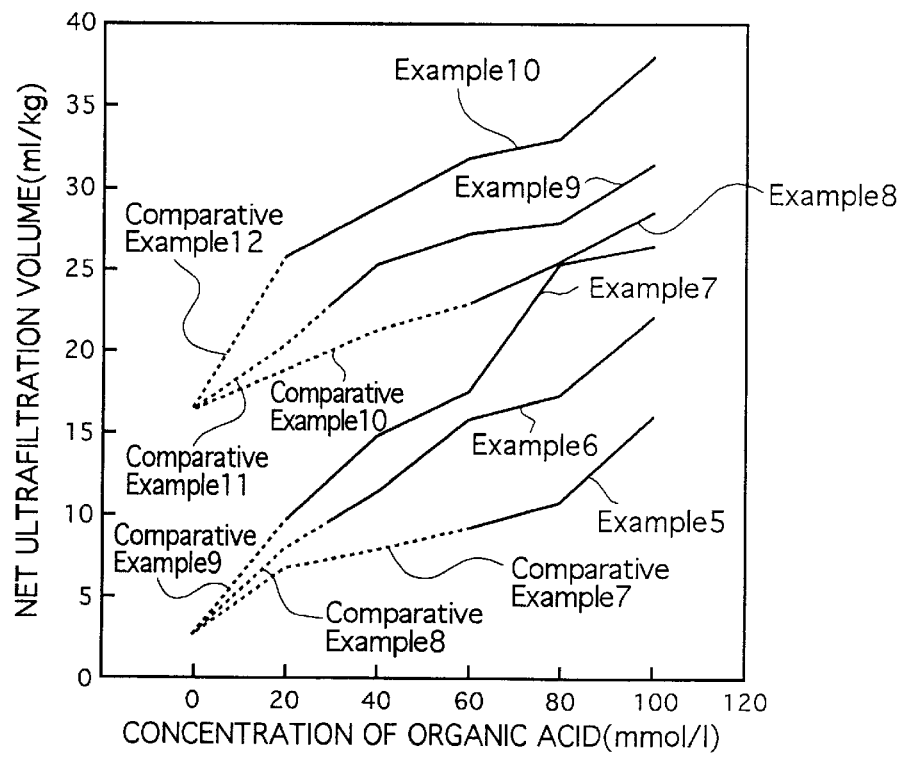
FIG. 5 is a graph illustrating the effect of peritoneal dialysis solution of the present invention.

(Results)
Net ultrafiltration volumes (after 6 hours' dwell) are shown in FIG. 5.

The results indicated that any of the organic acids gave larger net ultrafiltration volumes when the difference in concentration between the total cation and chloride ion is greater and the concentration of organic acid for maintaining electrical neutrality is higher.

Example 6 (the number of carbons in the organic acid: 6) had a larger net ultrafiltration volume than Example 5 (the number of carbons in the organic acid: 3), Example 7 (the number of carbon atoms in the organic acid: 7) had a larger net ultrafiltration volume than Example 6, Example 9 (the number of carbons in the organic acid: 6) had a larger net ultrafiltration volume than Example 8 (the number of carbons in the organic acid: 3), Example 10 (the number of carbons in the organic acid: 7) had a larger net ultrafiltration volume than Example 9, which indicated that the net ultrafiltration volume varied depending on the kind of organic acid and the greater the number of carbon atoms in the organic acid was, the more the net ultrafiltration volume was increased.

Figure 6:
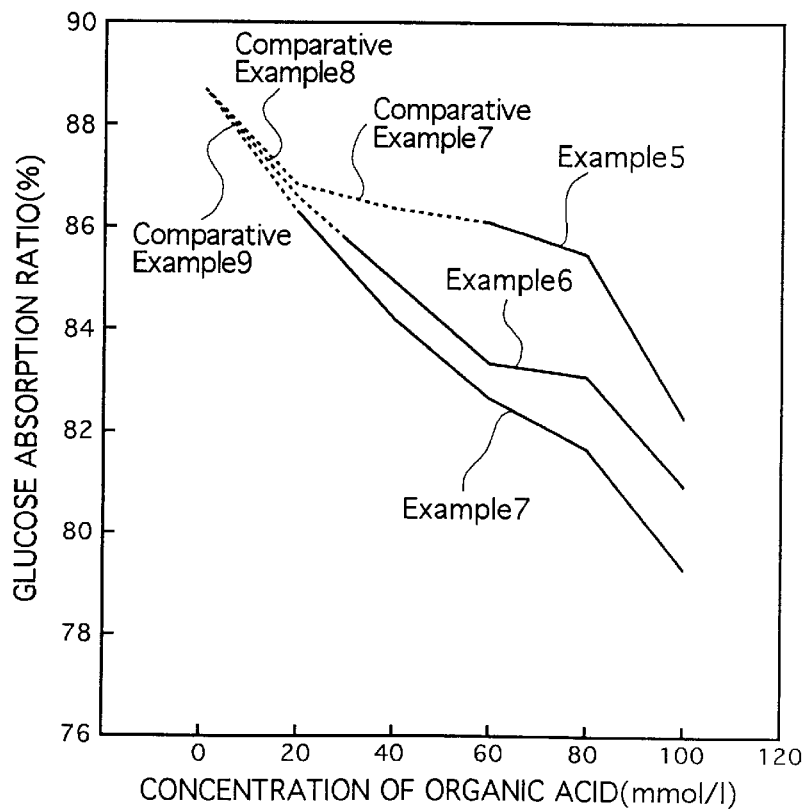
FIG. 6 is a graph illustrating the effect of peritoneal dialysis solution of the present invention.

Further, glucose absorption ratios of Examples 5 to 7 and Comparative examples 7 to 9 are shown in FIG. 6. The results demonstrated that the larger the difference in concentration between the total cation and chloride ion was and the higher the concentration of organic acid for maintaining electrical neutrality was, the more the glucose absorption ratio was decreased. Example 6 had a lower glucose absorption ratio than Example 5 and Example 7 than Example 6, which indicated that the glucose absorption ratio varied depending on the kind of organic acid and the greater the number of carbons in the organic acid was, the more the glucose absorption ratio was decreased.

Example 5

Study on the effects of the difference in concentration between the total cation and chloride ion and the kind (organic acid mixture) of organic acid for maintaining the electrical neutrality on the net ultrafiltration volume The Examples were practiced using peritoneal dialysis solutions containing 1.35 W/V % glucose.

(Preparation of Peritoneal Dialysis Solutions)

Glucose, sodium chloride, sodium lactate, ascorbic acid, N-acetyl-L-proline, and sodium hydroxide were dissolved in water for injection so that the reduced sugar, electrolyte ions, and organic acid ions would be of the concentrations shown in Table 5 to obtain peritoneal dialysis solutions of Examples 11 to 15 of the invention and Comparative Example 13.

The net ultrafiltration volume in each peritoneal dialysis solutions after 6-hour dwell time was measured in the same manner as in Example 1.

Results obtained are described together in Table 5.

TABLE 5

|  | Comparative Example 13 | Example 11 | Example 12 |
|---|---|---|---|
| Glucose (W/V %) | 1.35 | 1.35 | 1.35 |
| $Na^+$ (mEq/l) | 140 | 140 | 140 |
| $Cl^-$ (mEq/l) | 100 | 80 | 80 |
| Lactate ion (mmol/l) | 40 | 60 | 40 |
| Ascorbate ion (mmol/l) | 0 | 0 | 20 |

TABLE 5-continued

| N-Acetyl-L-proline ion (mmol/l) | 0 | 0 | 0 |
|---|---|---|---|
| Osmotic pressure (mOsm/kg) | 344 | 344 | 344 |
| Net ultrafiltration volume (ml/kg) | 8.0 | 9.2 | 10.3 |

|  | Example 13 | Example 14 | Example 15 |
|---|---|---|---|
| Glucose (W/V %) | 1.35 | 1.35 | 1.35 |
| $Na^+$ (mEq/l) | 140 | 140 | 140 |
| $Cl^-$ (mEq/l) | 80 | 80 | 80 |
| Lactate ion (mmol/l) | 30 | 20 | 30 |
| Ascorbate ion (mmol/l) | 30 | 40 | 0 |
| N-Acetyl-L-proline ion (mmol/l) | 0 | 0 | 30 |
| Osmotic pressure (mOsm/kg) | 344 | 344 | 344 |
| Net ultrafiltration volume (ml/kg) | 11.0 | 11.1 | 13.7 |

(Results)

As shown in Table 5, when the difference in concentration between the total cation and chloride ion is large, mixing of two kinds of organic acids were added for maintaining electrical neutrality, the net ultrafiltration volume was increased in the same manner as in the case where organic acids were used singly. Such results were the same when 3 or more kinds of organic acids were used as mixtures.

Example 6

Study on the effect of the difference in concentration between the total cation and chloride ion in the peritoneal dialysis solutions containing 3 kinds of cation components, i.e., sodium ion, calcium ion, and magnesium ion and the kind of organic acid (organic acid alone or mixtures thereof) for maintaining electrical neutrality on the net ultrafiltration volume and glucose absorption ratio (Preparation of Peritoneal Dialysis Solutions and Peritoneal Dialysis Test)

Glucose, sodium chloride, calcium chloride, magnesium chloride, sodium lactate, sodium glucuronate, N-acetyl-L-proline, N-acetyl-L-glutamine, and sodium hydroxide were dissolved in water for injection so that the reduced sugar, electrolyte ions, and organic acid ions would be of the concentrations shown in Table 6 to obtain peritoneal dialysis solutions of Examples 16 to 29 of the invention and Comparative Examples 14 and 15. The Examples and Comparative Examples were practiced using pertoneal dialysis solutions containing 1.35 W/V % and 0.72 W/V % glucose.

TABLE 6

| | Comparative Example 14 | Example 16 | Example 17 | Example 18 | Example 19 | Example 20 | Example 21 | Example 22 |
|---|---|---|---|---|---|---|---|---|
| Glucose (W/V%) | 1.35 | 1.35 | 1.35 | 1.35 | 1.35 | 1.35 | 1.35 | 1.35 |
| $Na^+$ (mEq/l) | 135 | 135 | 135 | 135 | 135 | 135 | 135 | 135 |
| $Ca^{2+}$ (mEq/l) | 2.5 | 2.5 | 2.5 | 2.5 | 2.5 | 2.5 | 2.5 | 2.5 |
| $Mg^{2+}$ (mEq/l) | 0.5 | 0.5 | 0.5 | 0.5 | 0.5 | 0.5 | 0.5 | 0.5 |
| $Cl^-$ (mEq/l) | 98 | 78 | 108 | 98 | 88 | 118 | 98 | 88 |
| Lactate ion (mmol/l) | 40 | 60 | | | | | | 40 |
| Glucuronate ion (mmol/l) | | | 30 | 40 | 50 | | | 10 |
| N-Acetyl-L-proline ion (mmol/l) | | | | | | 20 | 40 | |
| Osmotic pressure (mOsm/kg) | 337 | 337 | 337 | 337 | 337 | 337 | 337 | 337 |

| | Example 23 | Example 24 | Example 25 | Comparative Example 15 | Example 26 | Example 27 | Example 28 | Example 29 |
|---|---|---|---|---|---|---|---|---|
| Glucose (W/V%) | 1.35 | 1.35 | 1.35 | 0.72 | 0.72 | 0.72 | 0.72 | 0.72 |
| $Na^+$ (mEq/l) | 135 | 135 | 135 | 135 | 135 | 135 | 135 | 135 |
| $Ca^{2+}$ (mEq/l) | 2.5 | 2.5 | 2.5 | 2.5 | 2.5 | 2.5 | 2.5 | 2.5 |
| $Mg^{2+}$ (mEq/l) | 0.5 | 0.5 | 0.5 | 0.5 | 0.5 | 0.5 | 0.5 | 0.5 |
| $Cl^-$ (mEq/l) | 88 | 88 | 88 | 98 | 98 | 98 | 98 | 98 |
| Lactate ion (mmol/l) | 35 | 25 | 15 | 40 | | | 20 | 20 |
| Glucuronate ion (mmol/l) | 15 | 25 | 35 | | 40 | | 20 | |
| N-Acetyl-L-proline ion (mmol/l) | | | | | | 40 | | 20 |
| Osmotic pressure (mOsm/kg) | 337 | 337 | 337 | 299 | 299 | 299 | 299 | 299 |

Figure 7:
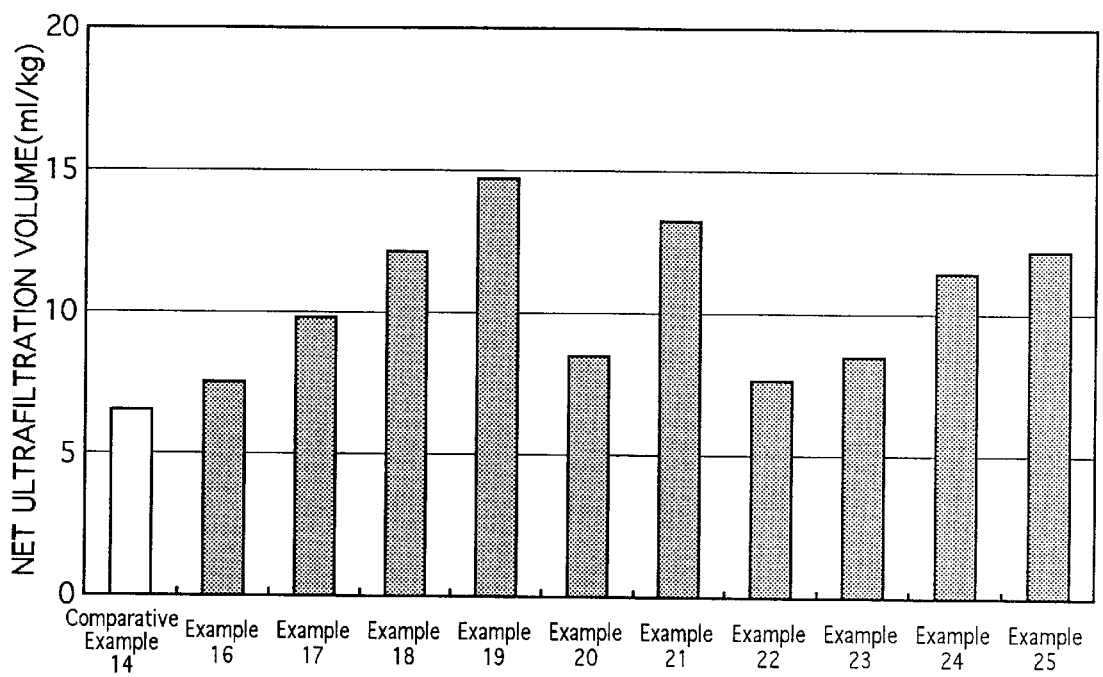
FIG. 7 is a graph illustrating the effect of peritoneal dialysis solution of the present invention.
Figure 8:
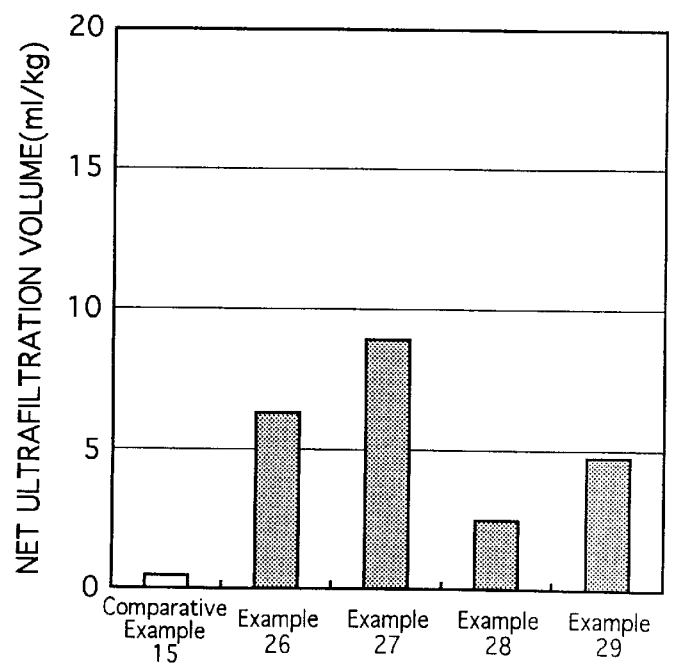
FIG. 8 is a graph illustrating the effect of peritoneal dialysis solution of the present invention.
Figure 9:
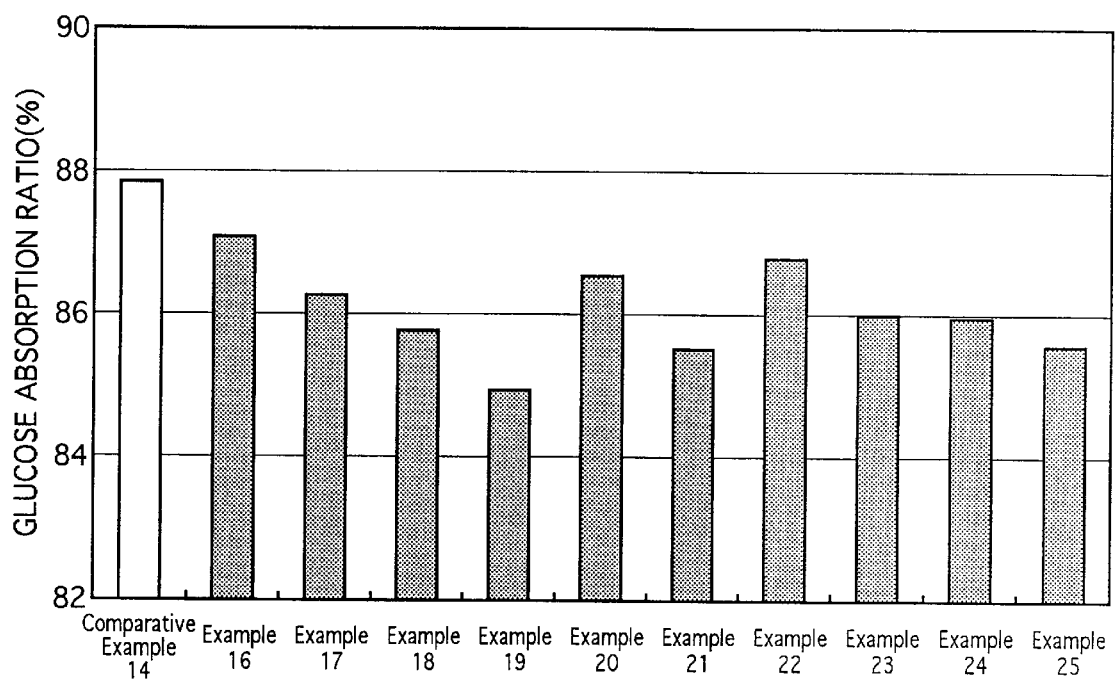
FIG. 9 is a graph illustrating the effect of peritoneal dialysis solution of the present invention.

The prepared peritoneal dialysis solutions were subjected to peritoneal dialysis tests in the same manner as Example 1. Examples 16 to 25 of the invention and Examples 26 to 29 of the invention were compared with Comparative Example 14 and Comparative Example 15, respectively. In the experiments, net ultrafiltration volume in each peritoneal dialysis solution after 6-hour dwell time, glucose absorption ratio (glucose absorption ratio being measured for the peritoneal dialysis solution at a glucose concentration of 1.35 W/V %) were compared and studied. The glucose absorption ratios were obtained in the same manner as in Example 4.
(Results)
The net ultrafiltration volume (after 6-hour dwell time) is shown in FIGS. 7 and 8.
(1) The results of Comparative Example 14 and Examples 16 to 21 demonstrated that when an organic acid was used alone, despite the peritoneal dialysis solutions at the same osmotic pressure and the same glucose concentration, each organic acid showed a larger net ultrafiltration volume at a greater difference in concentration between the total cation and chloride ion and at a higher concentration of organic acid for maintaining electrical neutrality.
(2) The results of Comparative Example 14 (the number of carbons in the organic acid: 3), Example 18 (the number of carbons in the organic acid: 6) and Example 21 (the number of carbons in the organic acid: 7), and the results of Comparative Example 15 (the number of carbons in the organic acid: 3), Example 26 (the number of carbons in the organic acid: 6) and Example 27 (the number of carbons in the organic acid: 7) demonstrate that even when the difference in concentration between the total cation and chloride ion was the same, the net ultrafiltration volume varied depending on the kind of organic acid and the larger the number of carbon atoms in the organic acid was, the more net ultrafiltration volume was increased.
Such effects were the same in the case where the difference in concentration between the total cation and chloride ion was other than 40 mEq/l.
(3) The results of Comparative Example 14 and Examples 22, 23, 24 and 25 and the results of Comparative Example 15 and Examples 28 and 29 demonstrate that even when two or more kinds of organic acid were used for maintaining electrical neutrality, like the case where the organic acids were used singly, the greater difference in concentration between the total cation and chloride ion resulted in an increased net ultrafiltration volume.
Such effects were the same in the case where 3 or more kinds of organic acids were mixed.
The effects shown in (1) to (3) above were the same when the osmotic pressure was varied by adjusting glucose concentration and/or electrolyte concentration.
Further, the effects shown in (1) to (3) above were the same when osmotic agents other than glucose were used. In this case, the same was true when the osmotic pressure was varied by adjusting glucose concentration and/or electrolyte concentration.
From the results described above, it can be said that the effects of the difference in concentration between the total cation and chloride ion in the peritoneal dialysis solution containing several kinds of cations such as sodium ion, calcium ion, and magnesium ion as the cation component and the kind of organic acid (organic acid alone or mixtures thereof) for maintaining electrical neutrality on the net ultrafiltration volume are the same as that of the peritoneal dialysis solution containing sodium ion alone as the cation (Examples 1 to 5).
Glucose absorption ratios of Comparative Example 14 and Examples 16 to 25 are shown in FIG. 9.
(4) The results of Comparative Example 14 and Examples 16 to 21 demonstrate that use of the organic acid alone resulted in a lower glucose absorption ratio with a greater difference in concentration between the total cation and chloride ion and a higher concentration of organic acid for maintaining electrical neutrality for each organic acid despite the fact that the peritoneal dialysis solutions had the same osmotic pressure and the same glucose concentration.

(5) Comparative Example 14 (the number of carbon atoms in the organic acid: 3), Example 18 (the number of carbon atoms in the organic acid: 6) and Example 21 (the number of carbon atoms in the organic acid: 7) demonstrate that even when the difference in concentration between the total cation and chloride ion was the same, different kind of organic acid resulted in different glucose absorption ratio and the greater the number of carbon atoms in the organic acid was, the lower the glucose absorption ratio was.

Such effects were the same in the case where the difference in concentration between the total cation and chloride ion was other than 40 mEq/l.

(6) The results of Comparative Example 14 and Examples 22 to 25 demonstrate that even when two or more kinds of organic acid for maintaining electrical neutrality were used, like the use of organic acid alone, the greater the difference in concentration between the total cation and chloride ion was, the lower the glucose absorption ratio was. Even when the difference in concentration between the total cation and chloride ion was the same, the greater the concentration ratio of organic acid having a larger number of carbon atoms was, the lower the glucose absorption ratio was.

Such effects were the same in the case where 3 or more kinds of organic acids were mixed.

The effects shown in (4) to (6) above were the same when the osmotic pressure was varied by adjusting glucose concentration and/or electrolyte concentration.

Further, the effects shown in (4) to (6) above were the same when osmotic agents other than glucose were used. In this case, the same was true when the osmotic pressure was varied by adjusting glucose concentration and/or electrolyte concentration.

From the above-described results, the effects of the present invention are apparent.

As described above, according to the peritoneal dialysis solution and the method for adjusting the peritoneal dialysis solution of the present invention, in which a difference in concentration is provided between the total cation and chloride ion and a predetermined concentration of organic acids for maintaining electrical neutrality is contained, there can be obtained a preferabe peritoneal dialysis solution having excellent performance of removing water, a prolonged effective dwell time and low glucose absorbability and in compliance with application such as the state of patients as compared with the conventional pertoneal dialysis solutions using glucose as the osmotic agent.

Therefore, according to the present invention, the net ultrafiltration volume and effective dwell time are secured at an osmotic pressure lower than the conventional peritoneal dialysis solutions and also the glucose absorption amount can be decreased, of the net ultrafiltration volume can be increased and the effective dwell time can be prolonged in peritoneal dialysis solutions having the same osmotic pressure.

What is claimed is:

1. A peritoneal dialysis solution comprising at least one cation;

a chloride ion at a concentration lower than the total concentration of said cation; and at least one organic acid which maintains electrical neutrality of the dialysis solution depending on the concentration difference between the total cation concentration and the chloride ion concentration, wherein the concentration of said at least one organic acid satisfies the following relation:

$$110 \geq A+B+C+D+E+F$$

$$A/60+B/50+C/40+D/30+E/20+F/10 \geq 1$$

wherein A (mmol/l) is total concentration of the organic acid having 3 carbon atoms, B (mmol/l) is total concentration of the organic acid having 4 carbon atoms, C (mmol/l) is total concentration of the organic acid having 5 carbon atoms, D (mmol/l) is total concentration of the organic acid having 6 carbon atoms, E (mmol/l) is total concentration of the organic acid having 7 carbon atoms, and F (mmol/l) is total concentration of the organic acid having 8 to 13 carbon atoms, and wherein said dialysis solution does not contain galactose.

2. The peritoneal dialysis solution as claimed in claim 1, wherein the concentration of chloride ion is 30 mEq/l to 180 mEq/l.

3. The peritoneal dialysis solution as claimed in claim 1, wherein the osmotic pressure of peritoneal dialysis solution is preferably 260 mOsm/kg to 600 mOsm/kg.

4. The peritoneal dialysis solution as claimed in claim 1, further comprising a glucose.

5. The peritoneal dialysis solution as claimed in claim 1, wherein the organic acid having 3 carbon atoms is at least one selected from the group consisting of lactic acid and propionic acid; the organic acid having 4 carbon atoms is at least one selected from the group consisting of malic acid, fumaric acid, succinic acid; oxaloacetic acid and N-acetylglycine, the organic acid having 5 carbon atoms is at least one selected from the group consisting of N-acetyl-L-cystein and glutaric acid; the organic acid having 6 carbon atoms is at least one selected from the group consisting of glucuronic acid, ascorbic acid, citric acid, isocitric acid, gluconic acid and N-acetyl-L-aspartic acid; the organic acid having 7 carbon atoms is at least one selected from the group consisting of N-acetyl-L-glutamic acid, N-acetyl-L-methionine, N-acetyl-L-proline and N-acetyl-L-valine; and the organic acid having 8 to 13 carbon atoms is at least one selected from the group consisting of N-acetyl-L-arginine, N-acetyl-L-histidien, N-acetyl-L-leucine and N-acetyl-L-tryptophane.

* * * * *